US012788245B2

(12) United States Patent
Alasaarela et al.

(10) Patent No.: US 12,788,245 B2
(45) Date of Patent: Nov. 10, 2026

(54) OPHTHALMIC EXAMINATION APPARATUS AND METHOD OF FORMING ALIGNMENT BETWEEN EYE AND OPHTHALMIC EXAMINATION APPARATUS

(71) Applicant: OPTOMED PLC, Oulu (FI)

(72) Inventors: Ilkka Alasaarela, Oulu (FI); Juho Pylvänäinen, Oulu (FI); Juha Lipponen, Oulu (FI); Seppo Rönkkö, Oulu (FI)

(73) Assignee: OPTOMED PLC, Oulu (FI)

( * ) Notice: Subject to any disclaimer, the term of this patent is extended or adjusted under 35 U.S.C. 154(b) by 627 days.

(21) Appl. No.: 18/258,543

(22) PCT Filed: Dec. 16, 2021

(86) PCT No.: PCT/FI2021/050887
§ 371 (c)(1),
(2) Date: Jun. 20, 2023

(87) PCT Pub. No.: WO2022/136732
PCT Pub. Date: Jun. 30, 2022

(65) Prior Publication Data

US 2024/0049964 A1 Feb. 15, 2024

(30) Foreign Application Priority Data

Dec. 21, 2020 (FI) ..................................... 20206350

(51) Int. Cl.
*A61B 3/15* (2006.01)
*A61B 3/00* (2006.01)

(52) U.S. Cl.
CPC ............ *A61B 3/152* (2013.01); *A61B 3/0025* (2013.01)

(58) Field of Classification Search
CPC ......... A61B 3/0025; A61B 3/107; A61B 3/14; A61B 3/12; A61B 5/14555; A61B 5/6821;
(Continued)

(56) References Cited

U.S. PATENT DOCUMENTS

| | | |
|---|---|---|
| 5,668,621 A | 9/1997 | Nanjo |
| 6,733,129 B2 | 5/2004 | Masaki |

(Continued)

FOREIGN PATENT DOCUMENTS

| | | |
|---|---|---|
| CN | 210582453 U | 5/2020 |
| EP | 1245182 A1 | 10/2002 |

(Continued)

OTHER PUBLICATIONS

International Search Report and Written Opinion of the ISA for PCT/FI2021/050887 mailed Mar. 14, 2022, 13 pages.

(Continued)

*Primary Examiner* — Brandi N Thomas
(74) *Attorney, Agent, or Firm* — Nixon & Vanderhye PC

(57) ABSTRACT

An ophthalmic examination apparatus comprises an alignment light generator, which directs beams of light from separate locations toward an image of an aperture stop of an imaging unit of the ophthalmic examination apparatus, and causes an envelope of the beams of light to converge to and diverge from a waist, which is within an alignment range of the ophthalmic examination apparatus. An eye is at an examination location with respect to the imaging unit when the waist of the envelope is located at least partly inside a pupil of the eye. The examination location of the ophthalmic examination apparatus is within the alignment range. The imaging unit receives reflections of the beams of light from a cornea of the eye within the alignment range, the eye being similar to a standard eye within standard tolerances. A user (Continued)

interface of the ophthalmic examination apparatus presents guidance information on a location of the eye with respect to the examination location based on locations of the reflections of the beams of light on a detecting surface of the imaging unit.

18 Claims, 10 Drawing Sheets

(58) Field of Classification Search
CPC ............. A61B 3/10; A61F 2009/00872; A61F 2009/00846
See application file for complete search history.

(56) References Cited

U.S. PATENT DOCUMENTS

| | | | | |
|---|---|---|---|---|
| 7,458,685 | B2 | 12/2008 | Liang et al. | |
| 10,307,058 | B2 | 6/2019 | Sakurada | |
| 10,321,822 | B1 | 6/2019 | Lee et al. | |
| 2002/0036749 | A1 | 3/2002 | Isogai | |
| 2006/0077346 | A1 | 4/2006 | Matsumoto | |
| 2012/0281185 | A1 | 11/2012 | Juhasz et al. | |
| 2013/0194548 | A1 | 8/2013 | Francis et al. | |
| 2016/0174838 | A1 | 6/2016 | Herranen et al. | |
| 2019/0254515 | A1 | 8/2019 | Zhang | |
| 2020/0085622 | A1 | 3/2020 | Scott et al. | |
| 2020/0100673 | A1 | 4/2020 | Shimizu et al. | |
| 2020/0245867 | A1 | 8/2020 | Pascal et al. | |
| 2023/0309826 | A1* | 10/2023 | Ashok | A61B 3/14 351/208 |

FOREIGN PATENT DOCUMENTS

| | | | | |
|---|---|---|---|---|
| EP | 2243421 | A1 | 10/2010 | |
| EP | 2564767 | * | 8/2012 | A61B 3/14 |
| EP | 2564767 | A1 | 3/2013 | |
| EP | 2949266 | A1 | 12/2015 | |
| EP | 3581088 | A1 | 12/2019 | |
| GB | 2451441 | A | 2/2009 | |
| WO | 2017025583 | A1 | 2/2017 | |

OTHER PUBLICATIONS

International Preliminary Report on Patentability for PCT/FI2021/050887 completed Apr. 21, 2023, 26 pages.

Finland Search Report for FI20206350 dated May 31, 2021, 2 pages.

Written Opinion of the International Preliminary Examining Authority for PCT/FI2021/050887 mailed Jan. 13, 2023, 7 pages.

* cited by examiner

OPHTHALMIC EXAMINATION APPARATUS AND METHOD OF FORMING ALIGNMENT BETWEEN EYE AND OPHTHALMIC EXAMINATION APPARATUS

CROSS-REFERENCE TO RELATED APPLICATIONS

This application is the U.S. national phase of International Application No. PCT/FI2021/050887 filed Dec. 16, 2021, which designated the U.S. and claims priority to FI 20206350 filed Dec. 21, 2020, the entire contents of each of which are hereby incorporated by reference.

FIELD

The invention relates to an ophthalmic examination apparatus and a method of forming an alignment between an eye and an ophthalmic examination apparatus.

BACKGROUND

A typical problem with ophthalmic instruments is how to align the instrument with patient's eye. The problem is particularly difficult with examination instruments which examine optically portions of an eye behind the iris, for example such as fundus cameras, where a wrong alignment may lead to dim and/or vignetted images and/or spurious reflections. Challenges in alignment are caused by a person whose eye is examined, eye movements of the person and from the fact that in many cases there is no precise enough way to know if the ophthalmic instrument is correctly aligned or not with respect to the eye that is examined.

Hence, an improvement to the alignment would be welcome.

BRIEF DESCRIPTION

The present invention seeks to provide an improvement in the measurements.

The invention is defined by the independent claims. Embodiments are defined in the dependent claims.

LIST OF DRAWINGS

Example embodiments of the present invention are described below, by way of example only, with reference to the accompanying drawings, in which FIG. 1 illustrates an example of an eye and its six degrees of freedom;

DESCRIPTION OF EMBODIMENTS

The following embodiments are only examples. Although the specification may refer to "an" embodiment in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may also contain features/structures that have not been specifically mentioned. All combinations of the embodiments are considered possible if their combination does not lead to structural or logical contradiction.

It should be noted that while Figures illustrate various embodiments, they are simplified diagrams that only show some structures and/or functional entities. The connections shown in the Figures may refer to logical or physical connections. It is apparent to a person skilled in the art that the described apparatus may also comprise other functions and structures than those described in Figures and text. It should be appreciated that details of some functions, structures, and the signalling used for measurement and/or controlling are irrelevant to the actual invention. Therefore, they need not be discussed in more detail here.

Figure 1:
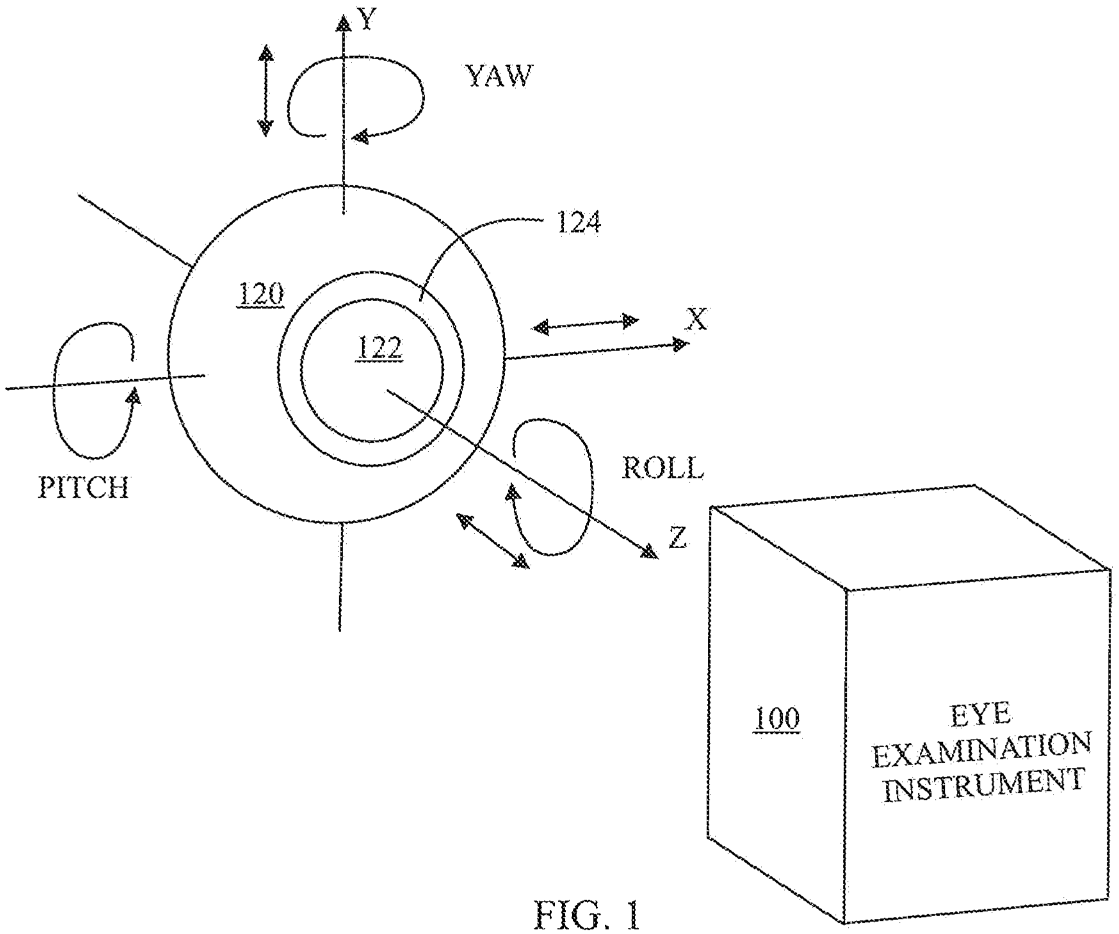

FIG. 1 illustrates an example of an eye 120 and its six degrees of freedom. Namely, the eye 120 may move back and forth along the spatial x-, y- and z-axis. Additionally, the eye 120 may rotate around the x-, y- and z-axis which can be defined in angular coordinates as pitch, yaw and roll. In this example, the x-axis denotes a horizontal axis, y-axis denotes a vertical axis and the z-axis denotes a horizontal axis between the eye 120 and the ophthalmic examination apparatus 100, the x-, y- and z-axes being orthogonal with respect to each other in this example.

In FIG. 1, the eye 120 of a person is in front of the ophthalmic examination apparatus 100. The eye 120 needs to be aligned in certain desired way relative to the ophthalmic examination apparatus 100, which is necessary in order to perform a proper examination with the ophthalmic examination apparatus 100.

Eye alignment means that the eye 120 has been oriented and positioned to match certain values or ranges of these coordinates. The targeted alignment accuracy for each dimension depends on the ophthalmic examination apparatus 100 and the use case.

The eye 120 contains a retina and approximately circular iris aperture, whose diameter may vary from a few millimeters up to 10 mm, typically between 3 and 8 mm, a crystalline lens and the cornea 116.

Sufficient horizontal and vertical alignments (yaw and pitch) may be arranged such that the ophthalmic examination apparatus 100 generates a fixation target in the person's field-of-view, and the person is instructed to aim his/her eyes to the fixation target. The fixation target may be arranged such that it guides the eye to a proper yaw and pitch angularly.

Proper rotational alignment (roll) may be achieved by the help of the set-up how the person is positioned in respect to the ophthalmic examination apparatus 100 as a whole. For example, if the person is standing or sitting, the roll-angle of the eye may be known with sufficient accuracy and ophthalmic examination apparatus 100 can be aligned accordingly. For further adjusting the roll-angle, the ophthalmic examination apparatus 100 may also generate a target figure in the person's field-of-view, and the person is instructed to rotate his/her head such that the target figure is in a certain rotation. In many ophthalmic examination apparatuses 100, such as fundus cameras, the accurate alignment of roll is not needed but a rough roll alignment is enough.

For achieving a proper spatial xyz-alignment, the ophthalmic examination apparatus 100 generates at least two beams 104, 104' which reflect from the cornea. The reflected beams may then be captured by one or more sensors in the ophthalmic examination apparatus 100. The visibility of the beams in those sensors, and the positions of the reflected beams on the detecting surface 114, may be used to compute needed corrective alignment movements.

The calculated alignment instructions can be given to the person whose eye is examined, and he/she can then correct the eye alignment. Or, the instructions may be given to an operator of the ophthalmic examination apparatus 100, who can correct the alignment. Or, an automated alignment mechanism can use the calculated instructions for performing an alignment between the ophthalmic examination apparatus 100 and the eye automatically.

These arrangements are now described in more detail below.

Figure 2:
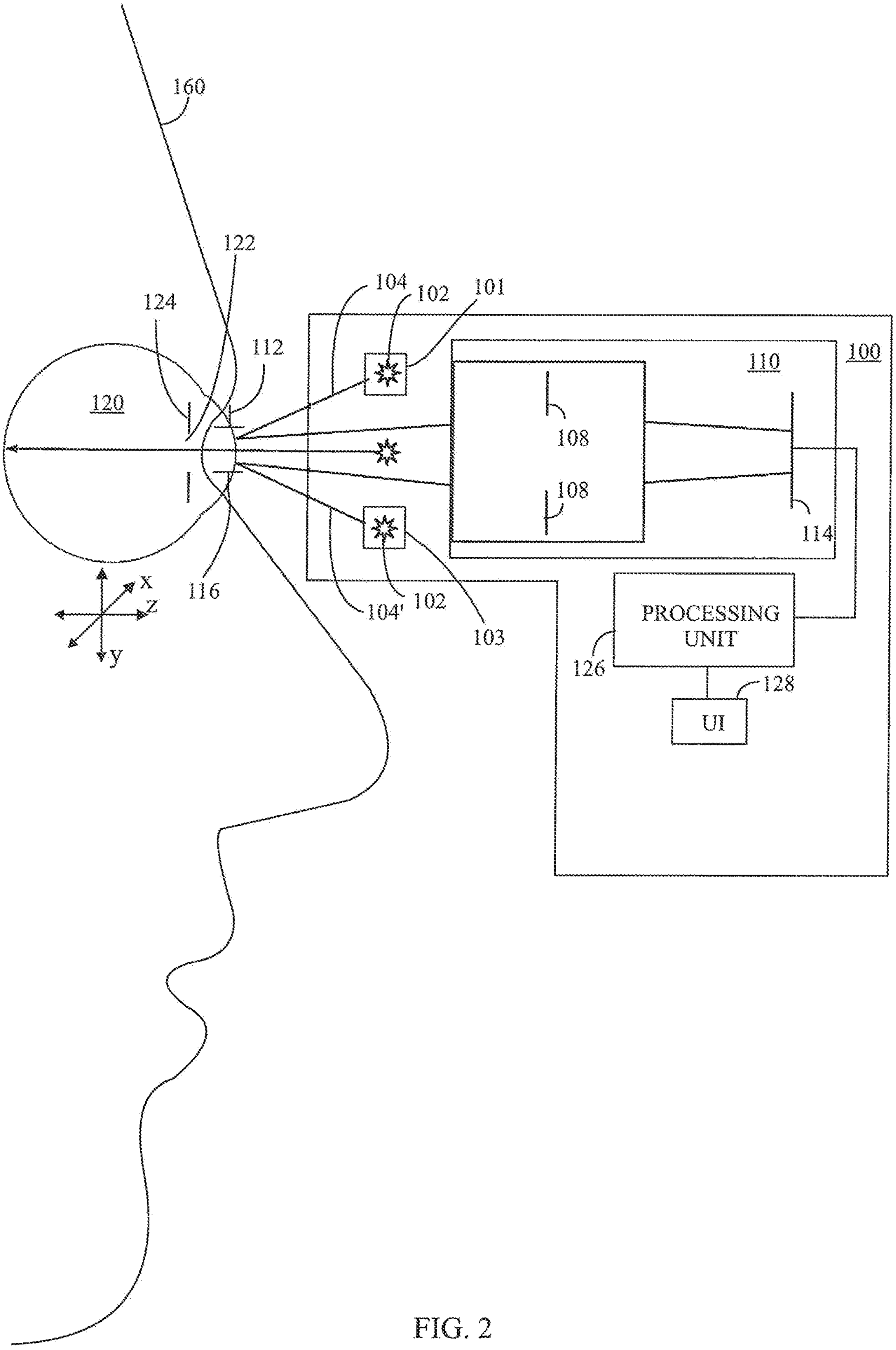
FIG. 2 illustrates an example where an eye is in front of an ophthalmic examination apparatus.

FIG. 2 illustrates an example where an eye is in front of the ophthalmic examination apparatus 100. The ophthalmic examination apparatus 100 comprises an alignment light generator 102, which directs beams toward cornea 116 such that when eye 120 is located at the examination location 118 reflected rays from the cornea 116 propagate virtually from inside the an image 112 of an aperture stop 108, i.e. if lines of the reflected rays are continued into the eye 120, the lines propagate through the image 112 of an aperture stop 108 inside the eye 120 (see also FIGS. 6 to 9). Alternatively it may be considered that the alignment light generator 102 directs beams 104, 104' of light from separate locations 101, 103 toward an image 112 of an aperture stop 108 of an imaging unit 110 of the ophthalmic examination apparatus 100.

Figure 5A:
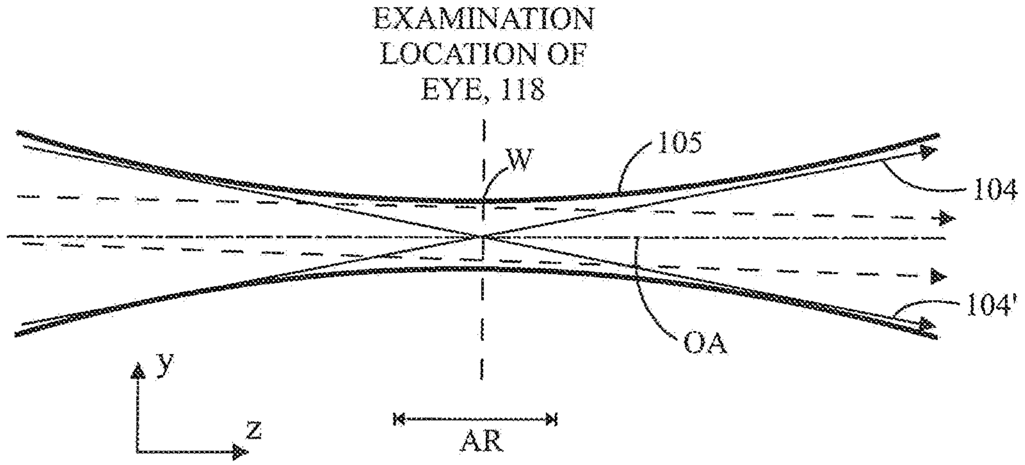
FIG. 5A illustrates an example of envelope of beams.

In an embodiment, a cross sectional area of a beam 104, 104' at or adjacent to the waist W, a normal of the cross section being parallel to propagation of the beam, may be in a range from about 1 $mm^2$ to about 8 $mm^2$, for example (waist W can be seen in FIG. 5A). In an embodiment, a cross sectional area of a beam 104, 104', a normal of the cross section being parallel to propagation of the beam, may be about 3 $mm^2$, for example. A shape of the beam 104, 104' may be a circle, an ellipse, a square, a rectangle or the like, for example. The image 112 of the aperture stop 108 of the imaging unit 110 is in front of the ophthalmic examination apparatus 100 and the imaging unit 110. The alignment light generator 102 causes an envelope 105 of the beams 104, 104' of light to converge to and diverge from a waist W, which is within an alignment range AR of the ophthalmic examination apparatus 100, which is illustrated in FIG. 5A. The waist W and the alignment range AR are in front of the ophthalmic examination apparatus 100 and the imaging unit 110 in a direction of an optical axis OA of the imaging unit 110 and/or the ophthalmic examination apparatus 100.

The eye 120 is at an examination location 118 with respect to the imaging unit 110 when the waist W of the envelope 105 is located at least partly inside a pupil 122 of the eye 120 or when the cornea 116 is located within the alignment range AR at about the waist W. In an embodiment, the waist W may be or may be meant to be fully inside the pupil 122 of the eye 120. The ophthalmic examination apparatus 100 naturally has the examination location 118 within the alignment range AR. The examination location 118 can be understood to be a location where the eye examination and/or achieved results of the eye examination lead/leads to an expected resolution, is/are within expected limits and quality can be considered normal and/or at least satisfactory. The examination location 118 has a narrow range which can be considered a tolerance within which the examination of eye 120 can be performed normally and properly.

The imaging unit 110 receives reflections of the beams 104, 104' of light from a cornea 116 of the eye 120, when the eye 120 is within the alignment range AR. The measures and design of the ophthalmic examination apparatus 100 are based on a principle that the eye 120 is assumed to be at least to a certain extent similar to a standard eye within standard tolerances of the standard eye.

The standard eye may be based on an Emsley model, Emsley-Gullstrand model, or Liou and Brennan schematic eye model, for example. The eye model may be similar to an anatomical and optical eye. It may have a power of about 60.4 D and an axial length of about 24 mm for example. The eye model may estimate aberrations in a visible range of light. In an embodiment, the eye model may have variation depending on a size of a person 160 that is examined, sex and age especially when it is a question of a child, for example. That is, the eye model may be selected based on anatomical and/or optical information on the person 160 to be examined.

A user interface 128 of the ophthalmic examination apparatus 100 presents, directly or indirectly, a person 160, whose eye 120 is examined, and/or an operator guidance information on a location of the eye 120 with respect to the examination location 118 based on locations of the reflections of the beams 104, 104' of light on a detecting surface 114 of the imaging unit 110. The guidance information may be an image how spots of light are distributed on a detecting surface 114 of the imaging unit 110 (see FIG. 13).

A processing unit 126 of the ophthalmic examination apparatus 100 may provide, directly or indirectly, the person 160, whose eye 120 is examined, and/or the operator with the guidance information on a location of the eye 120 with respect to the examination location 118 based on locations of the reflections of the beams 104, 104' of light on the detecting surface 114 of the imaging unit 110. This information may be more processed than mere information in the form of an image of the spots 400 on the detecting surface 114 and may include symbols of a writing system such as alphabets, kanji-signs and/or numbers. The operator may be a human being or a machine. The machine may be an artificial intelligence machine, for example. The information may include arrows, colors, lines, dots, circles, any combination of these, or the like, for example.

In an embodiment, the processing unit 126 forms the guidance information based on the locations of the reflections of the beams 104, 104' with respect to each other. In an embodiment, the processing unit 126 forms the guidance information based on a distance between the locations of the reflections of the beams 104, 104'. In an embodiment, a first reflection of one of the beams 104, 104' is detected with a first detecting surface element and a second reflection of the another of the beams 104, 104' is detected with a second detecting surface element, a distance between the first detecting surface element and the second detecting surface element being known and/or determined, and the processing unit 126 forms the guidance information based on the locations of the reflections of the beams 104, 104' on the first and second detecting surface elements and the distance between the first and second detecting surface elements.

In general, the alignment light generator 102 comprises at least one light source 102'. The at least one light source 102' may output near-infrared light such that the wavelength range distracts the person whose eye 102 is examined less than if the light contained mostly visible light. In an embodiment, a dominating wavelength band may be from about 700 to about 1100 nm, for example. In an embodiment, a dominating wavelength band may be from about 750 to about 970 nm, for example. The at least one light source 102' may comprise one or more light emitting diodes (LED), organic light emitting diodes (OLED), one or more incandescent light sources, and/or one or more lasers, and/or any kind of light source capable of emitting light at least partially in the desired wavelength range. The at least one light source 102' may comprise a filter for band-pass filtering a desired wavelength band.

Figure 3:
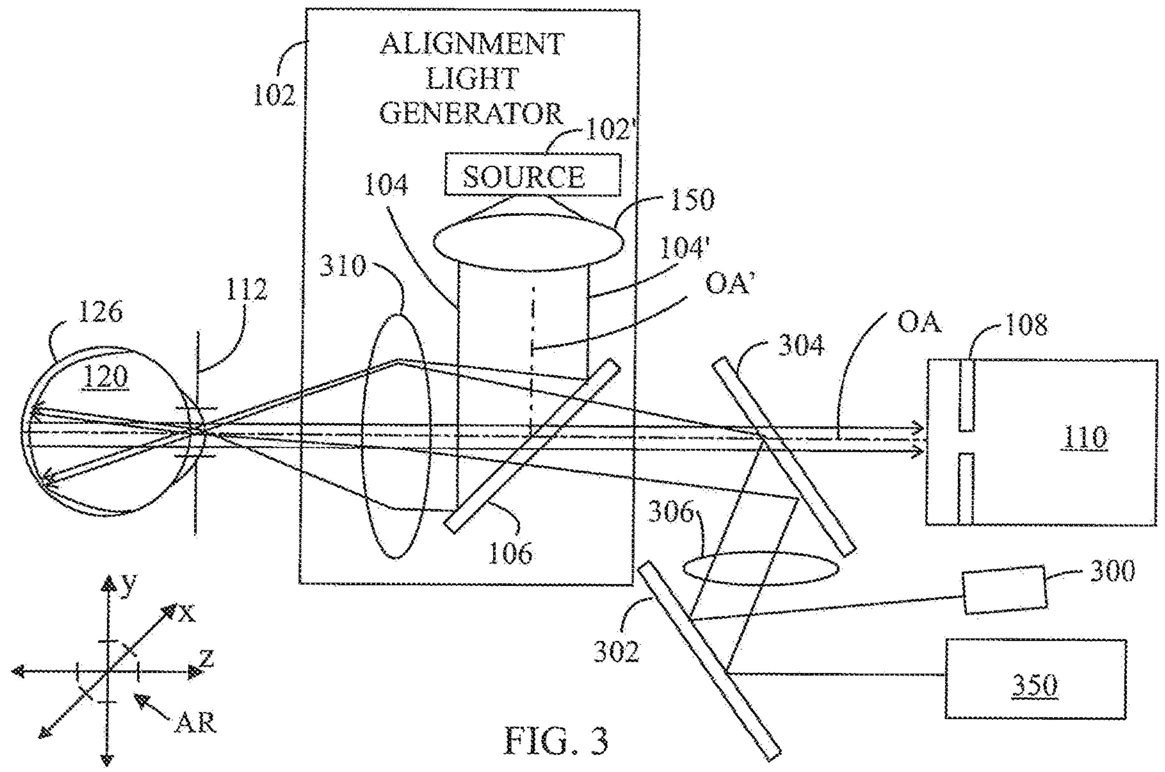
FIG. 3 illustrates an example of the ophthalmic examination apparatus.

FIG. 3 illustrates an example of the ophthalmic examination apparatus 100. The alignment light generator 102 may also comprise at least one initial lens 150 in an embodiment. Any of the at least one initial lens 150 may be an image forming lens, for example. Alternatively or additionally to the at least one initial lens 150, the alignment light generator 102 may comprise at least one mirror. Any of the at least one mirror may be an image forming mirror, for example. In an embodiment, the at least one initial lens 150 may collimate the beams 104, 104' of light with respect to each other, for example. In such a case, a projection of any one of the beams 104, 104' on a plane, a normal of which is perpendicular to the optical axis of the alignment light generator 102, is parallel to a projection of any other of the beams 104, 104' on said plane within an aberration tolerance. In this embodiment, the alignment light generator 102 may direct the beams 104, 104' of light via a beam splitter 106 toward the image 112 of the aperture stop 108.

Figure 4A:
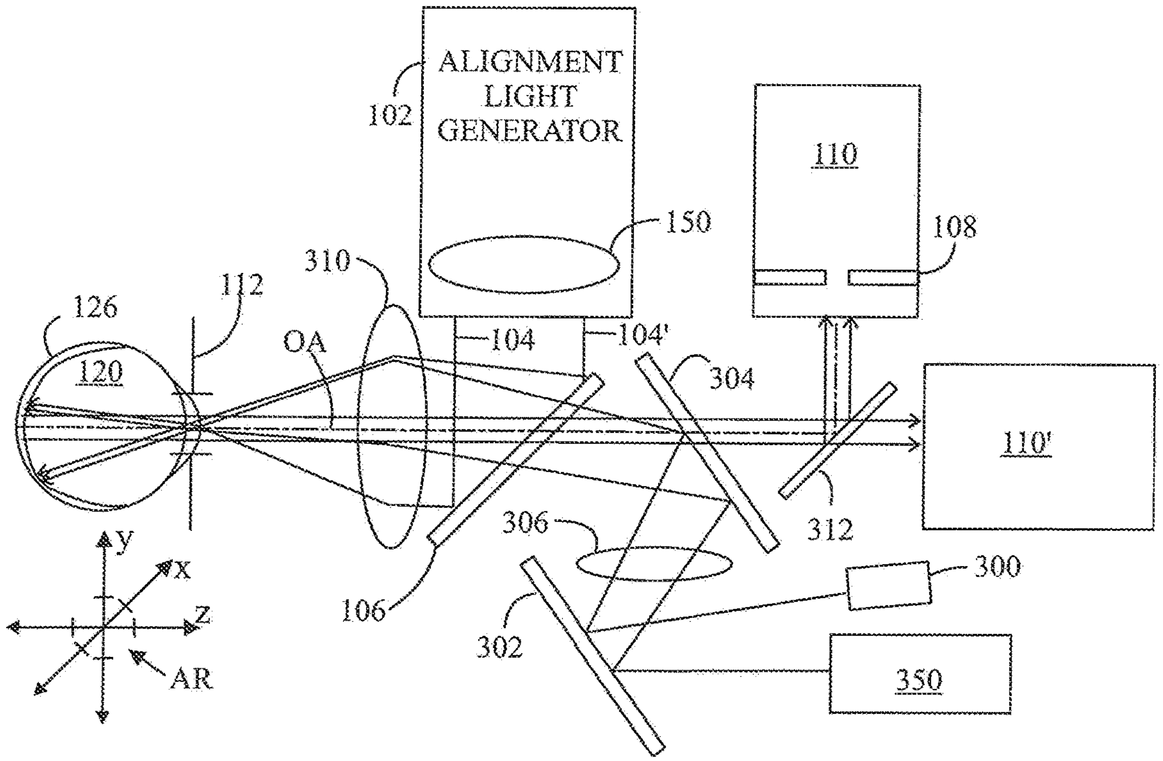
FIG. 4A illustrates another example of the ophthalmic examination apparatus.

After the beam splitter 106 in a direction of propagation from the alignment light generator 102 toward the eye 120, the beams 104, 104' of light may be pass through at least one objective lens 310. The at least one objective lens 310 may be common to the alignment light generator 102 and the imaging unit 110 like in the example of FIGS. 3 and 4A. In an embodiment, the alignment light generator 102 and the imaging unit 110 may have separate objective lenses, although their optical axes OA, OA' should have a determined and known relation to each other in order to enable the alignment between the eye 120 and the imaging unit 110. The optical axis OA' of the alignment light generator 102 and the optical axis OA of the imaging unit 110 may be at least approximately coaxial between the eye 120 and the ophthalmic examination apparatus 100. The optical axis OA' of the alignment light generator 102 and the optical axis OA of the imaging unit 110 may be at least approximately coaxial between the eye 120 and the beam splitter 106.

The at least one objective lens 310 may cause an envelope 105 of the beams 104, 104' of light to converge to and diverge from the waist W. In this manner, the beams 104, 104' of light approach each other and the optical axis OA. However, the beams 104, 104' of light do not necessarily intersect each other. In an embodiment, at least two of the beams 104, 104' of light intersect each other and/or the optical axis OA. This convergence can be caused together with the at least one initial lens 150 and the objective lens 310 in this example. Alternatively particularly in an embodiment when the alignment light generator 102 and the imaging unit 110 may have separate objective lenses, the convergence may be caused alone by the at least initial lens 150, at least one image forming optical component 300 or by a light manipulation arrangement 254, which is not image forming (see FIG. 14).

The at least one image forming optical component 300 may comprise one of more optically refractive and/or reflective components which may form a real image or a virtual image. The one of more optically refractive and/or reflective components may comprise at least one lens and/or mirror, which has a curved surface.

Any of the at least one objective lens 310 may be an image forming lens, for example. Alternatively or additionally to the at least one objective lens 310, the alignment light generator 102 may comprise at least one mirror. Any of the at least one mirror may be an image forming mirror, for example.

Figure 4B:
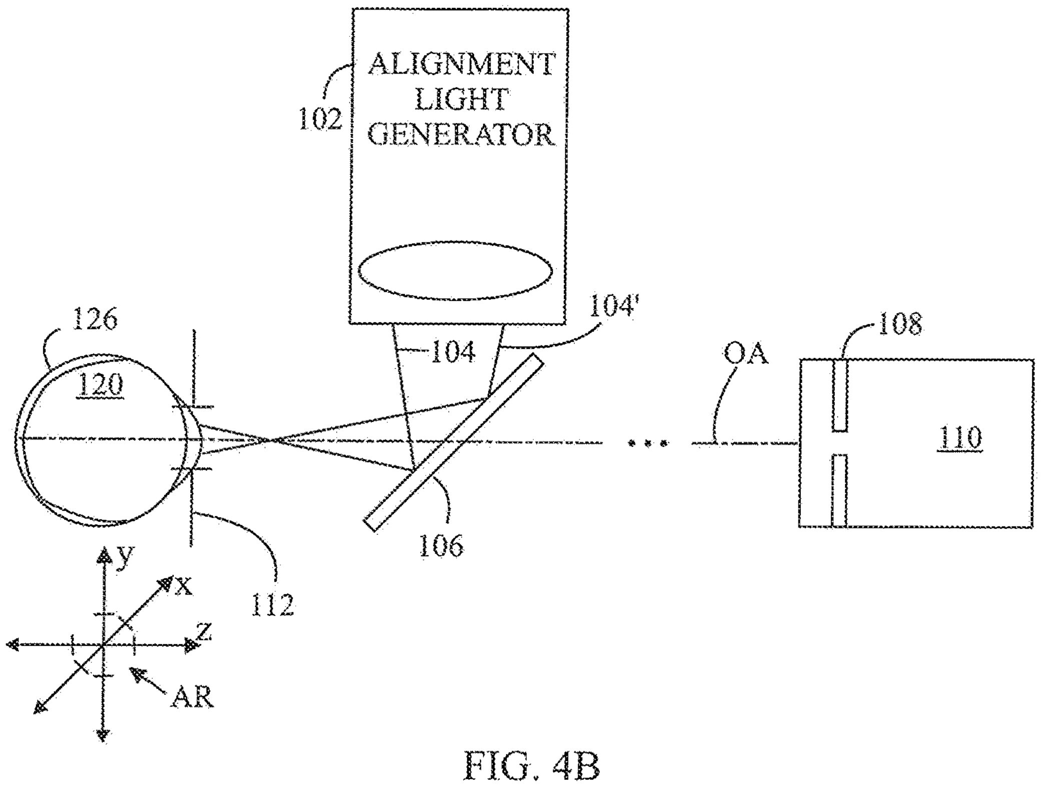
FIG. 4B illustrates still another example of the ophthalmic examination apparatus.

FIG. 4B illustrates an example where the beam splitter 106 is located in front of image forming optical components of the imaging unit 110. In this example, the at least one initial lens 150 makes the beams 104, 104' converge. The optical arrangement behind the three dots on the side of the imaging unit 110 may be similar to that of FIG. 3 or FIG. 4A.

The imaging unit 110 may comprise one of more optically refractive and/or reflective components which may form a real image or a virtual image. The one of more optically refractive and/or reflective components may comprise at least one lens and/or mirror, which has a curved surface.

Figure 6:
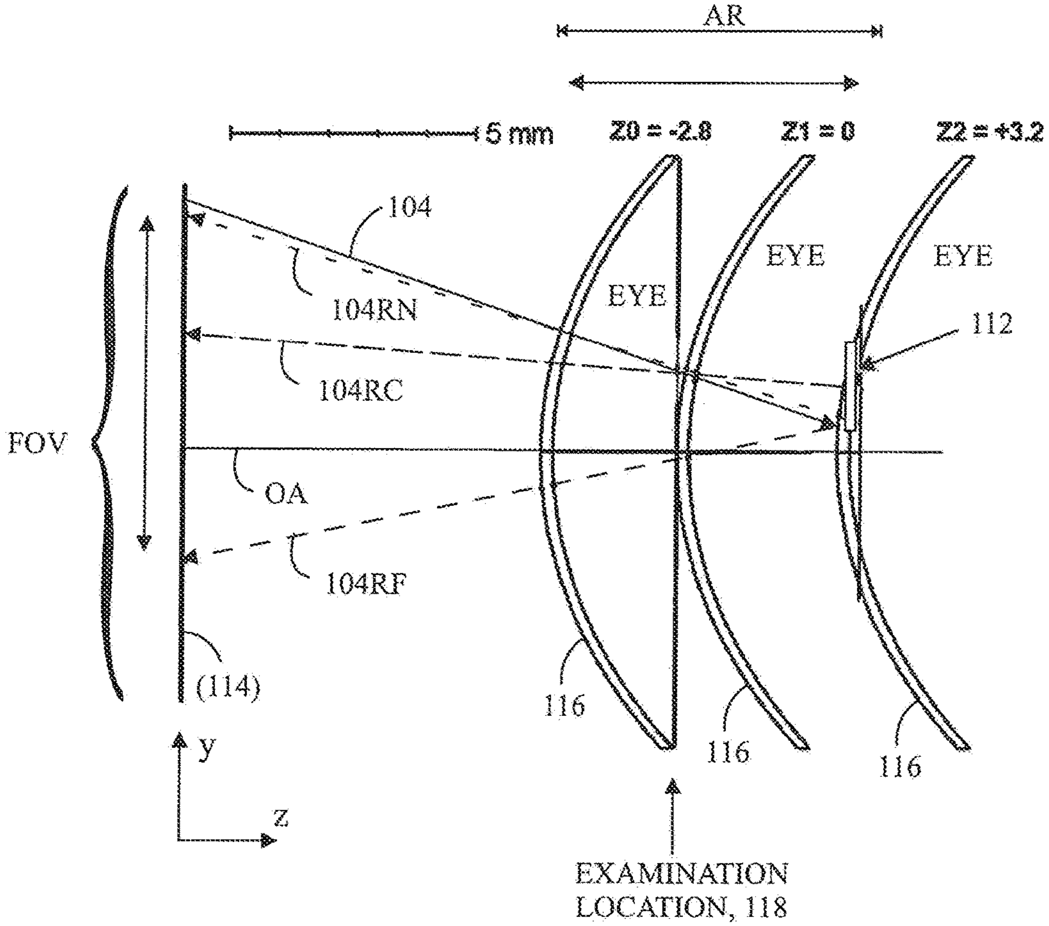
FIG. 6 illustrates an example where an eye moves from one side of the examination location to another side of the examination location in z-axis in an yz-plane.

FIG. 6 illustrates an example where the eye 120 moves from a location Z0=−2.8 mm, which is too close to the ophthalmic examination apparatus 100, through the examination location 118, Z1=0 mm, where the examination of the eye 120 can be performed, to a location Z2=+3.2 mm, which is too far from ophthalmic examination apparatus 100. The numbers mean a distance between the examination location 118 and the actual location of the ophthalmic examination apparatus 100 in this example. That the first number (−2.8 mm) has a minus-sign means that the ophthalmic examination apparatus 100 is too close to the eye 120. Correspondingly that the second number (+3.2 mm) is positive means that the ophthalmic examination apparatus 100 is too far from the eye 120.

When the distance between the eye 120 and the ophthalmic examination apparatus 100 is too short for a proper examination, the beam 104 and its reflection 104RN (Reflection Near) from the cornea 116 are almost parallel in this example.

When the distance between the eye 120 and the ophthalmic examination apparatus 100 is correct for a proper examination, the reflection 104RC (Reflection Correct) of the beam 104 from the cornea 116 is almost parallel to the optical axis OA in this example.

When the distance between the eye 120 and the ophthalmic examination apparatus 100 is too long for a proper examination, the reflection 104RC (Reflection Far) of the beam 104 from the cornea 116 deviates strongly from the beam 104 and the optical axis OA.

It can also be seen in FIG. 6 that the beam 104 in the alignment range AR hit the cornea 116 such a way, that the reflected beam seems to propagate through the image 112 of the aperture stop 108 of the imaging unit 110 (the dashed lines continue up to the image 112 of the aperture stop 108), although at the locations Z0=−2.8 mm and Z2=+3.2 mm that takes place near the border of the image 112 of the aperture stop 108. The beam 104 in the examination location 118, Z1=0 mm hit in the middle of the image 112 of the aperture stop 108 of the imaging unit 110 in this example.

When the reflections of the beams 104, 104' of light seem to propagate through the image 112 of the aperture stop 108 of the imaging unit 110, the reflected beams also may pass the aperture stop 1080 of the imaging unit 110.

When the reflection of the beam 104 is directed in different directions as a function of a distance between the eye 120 and the ophthalmic examination apparatus 100 or at least the imaging unit 110, the different directions translate into different positions on the detecting surface 114 which is illustrated in FIG. 6 with the reference number 114, which is in parenthesis. When the reflections of the beams 104, 104' of light remain within the field-of-view FOV of the imaging unit 110, the reflections also remain on detecting surface 114. Note that a location of the image 112 of the aperture stop 108 may deviate from the middle of the cornea 116 or the pupil 122 of the eye 120 in this cross sectional plane.

Figure 7:
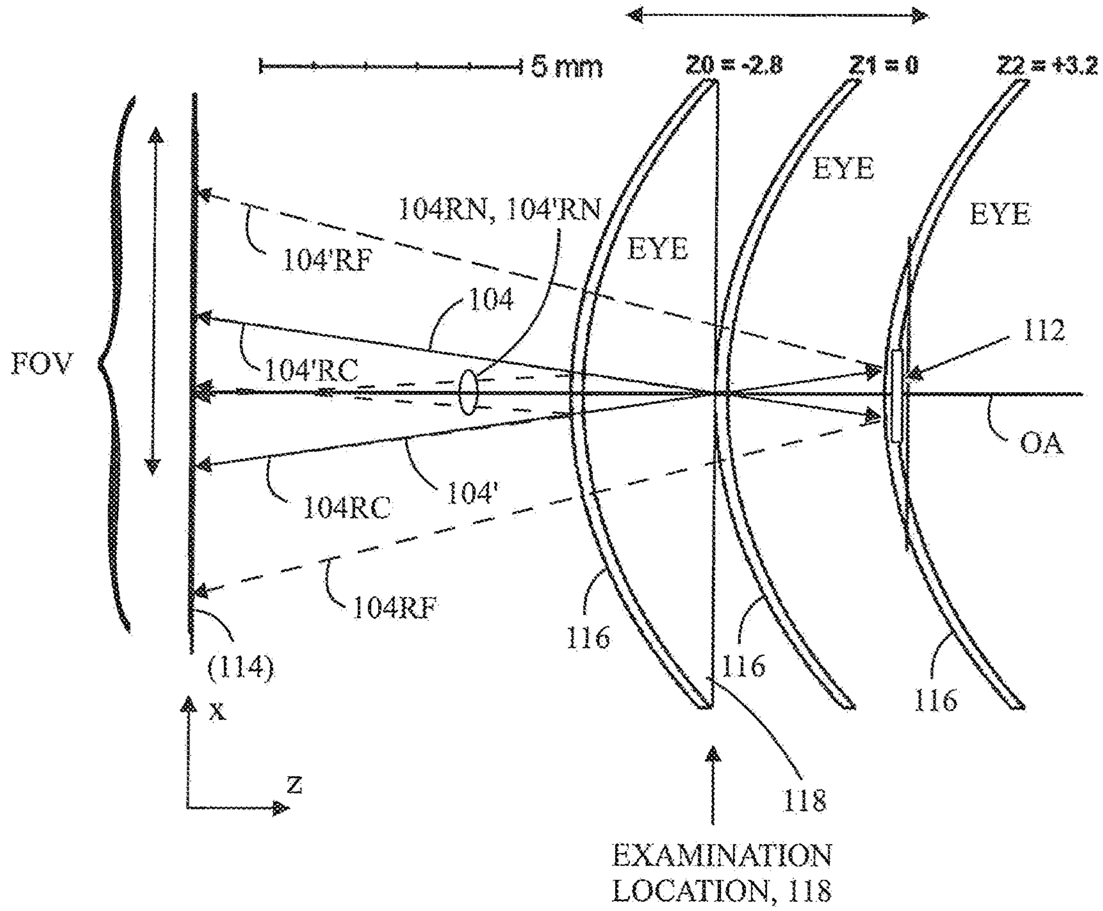
FIG. 7 illustrates an example where an eye moves from one side of the examination location to another side of the examination location in z-axis in an xz-plane.

FIG. 7 illustrates an example which can be considered the same as that of FIG. 6. However, FIG. 7 illustrates an orthogonal cross sectional plane to that of FIG. 6. It can been seen that the beams 104, 104' are differently distributed about the optical axis OA compared with FIG. 6. The beam 104 or its projections reflects parallel to and on the beam 104' or its projection, and vice versa, on this plane (line 104 is the same as 104'RC), when the eye 120 is at the examination location 118, Z1=0 mm.

When the eye 120 is too near the ophthalmic examination apparatus 100 at the location Z0=−2.8 mm, the reflections 104RN, 104'RN of the beams 104, 104' are close to the optical axis OA.

When the eye 120 is too far from the ophthalmic examination apparatus 100 at the location Z2=+3.2 mm, the reflections 104RF, 104'RF of the beams 104, 104' are close to the extremes of the field-of-view FOV and hit close to the edges of the detecting surface 114.

Figure 8:
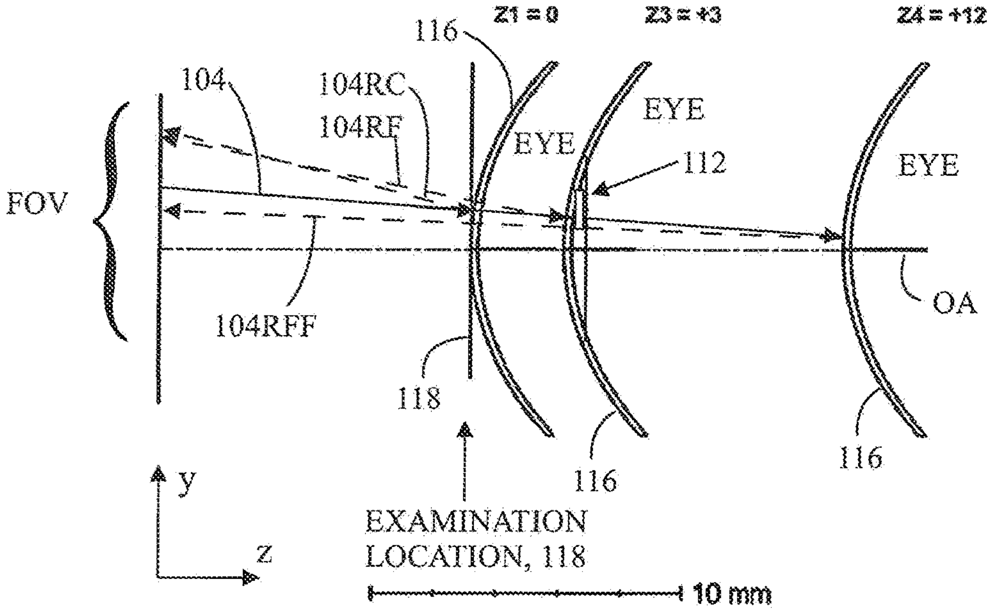
FIG. 8 illustrates an example where an eye moves from one side of the examination location to a location far too far on another side of the examination location in z-axis in an yz-plane.

FIG. 8 illustrates an example where the cornea 116 of the eye 120 is particularly far from the examination location 118 and the ophthalmic examination apparatus 100 at Z4=+12 mm. FIG. 8 illustrates the situation in an yz-plane. When at least one of the beams 104 has a small angle with respect to the optical axis OA eye 120 and/or the imaging unit 110, the alignment range AR may be made large.

Figure 9:
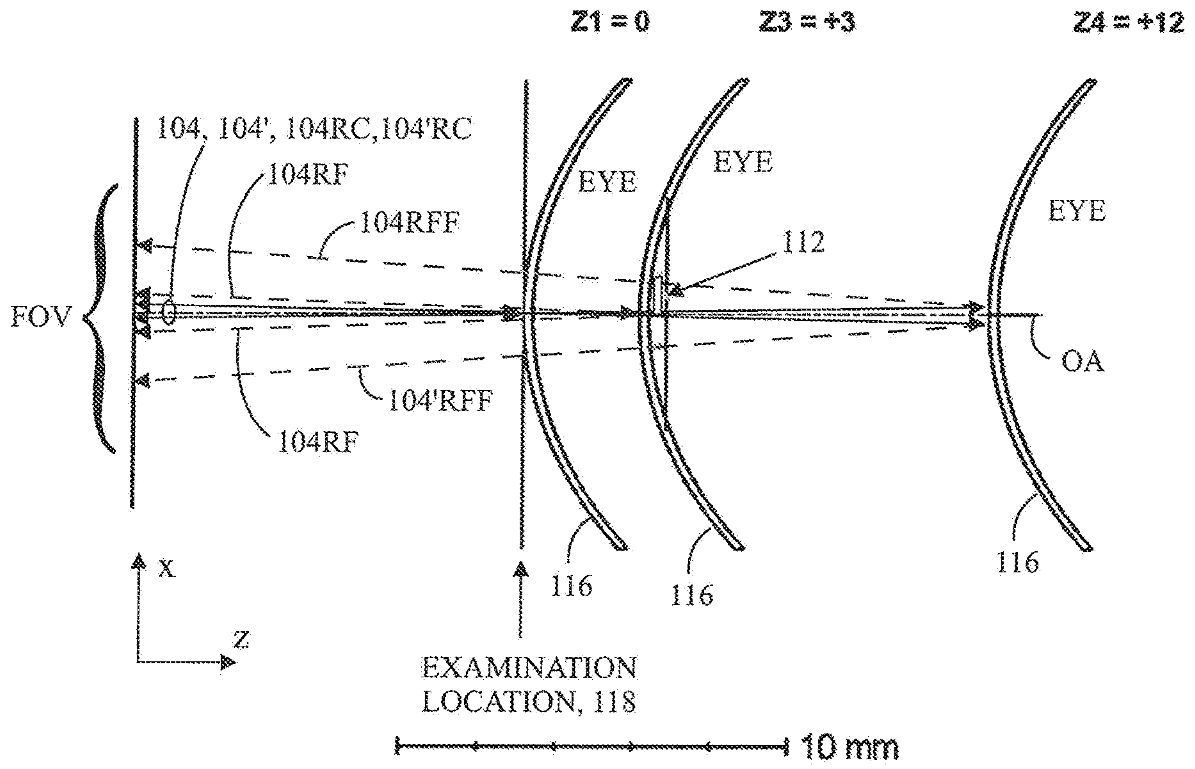
FIG. 9 illustrates an example where an eye moves from one side of the examination location to a location far too far on another side of the examination location in z-axis in an xz-plane.

FIG. 9 illustrates an example that is similar to that of FIG. 8 in a xy-plane which is perpendicular to the yz-plane. In this case, the beams 104, 104' may have even a smaller angle with respect to the optical axes OA of the eye 120 and/or the imaging unit 110.

Now referring to FIGS. 6, 7, 8 and 9, the beams 104 and 104' are arranged according to similar conditions, which may be defined as follows:

- the continuations of the reflected rays 104RC, 104RF, 104RFF, 104'RC, 104'RF, 104'RFF, which are depicted using dashed lines, pass through the image 112 of the aperture, here 104RC, 104'RC mean beams reflected from the examination location 118 (Reflection Correct), 104RF, 104'RF mean beams reflected from a location far and/or beyond from the examination location (Reflection Far), 104RFF, 104'RFF mean beams reflected from a location farther than the beam 104'RF (Reflection Further Far),
- the reflected beams 104RC, 104RF, 104RFF, 104'RC, 104'RF, 104'RFF are within the FOV of the imaging unit 110
- beams 104 and 104' have a non-zero angle with respect to each other although they are approximately parallel in yz-plane, the non-zero angle may be about 2° to about 40°, for example, without limiting to this range
- beams 104 and 104' are approximately symmetrical about z-axis in xz-plane, which may be considered mirror symmetrical about z-axis in xz-plane
- beams 104 and 104' intersect approximately at the surface of the cornea 116 at the examination location 118, Z1.

All of these conditions apply simultaneously.

In FIG. 9, beams 104, 104', 104RC, 104'RC are so close to each other that they have not been marked separately. A line of the beam 104 toward the cornea 116 is above the optical axis OA, and a line of the beam 104' toward the cornea 116 is below the optical axis OA. A line of the reflected beams 104RC is on the line of the beam 104', and a line of the reflected beam 104'RC is on the line of the beam 104.

Note that the depicted arrangement may also have the following properties:

- usable z-range that is between the eye 120 and the ophthalmic examination apparatus 100 extends further outward from the location Z2=+3.2 mm than inward from the examination location 118, Z1=0 mm (i.e. allows alignment method to be used farther when the eye 120 is further from the ophthalmic examination apparatus 100)
- the angles between the beams 104, 104' with respect to z (in eye front coordinates, see FIG. 16) are smaller compared to what is presented in FIG. 7, which leads to somewhat less accurate alignment, but increases the spatial range (longer z-range in particular) where the alignment method is usable.

The ophthalmic examination apparatus 100 can thus guide the eye 120 toward the examination location when the eye 120 is far too far (Z4=+12 mm) from the ophthalmic examination apparatus 100 at first as illustrated in FIGS. 8 and 9. Also here the values 0 mm, +2.8 mm and +12 mm may, for example, be understood to be additional distances to the examination location 118, which is a predetermined distance between the eye 120 and the ophthalmic examination apparatus 100.

Figure 10:
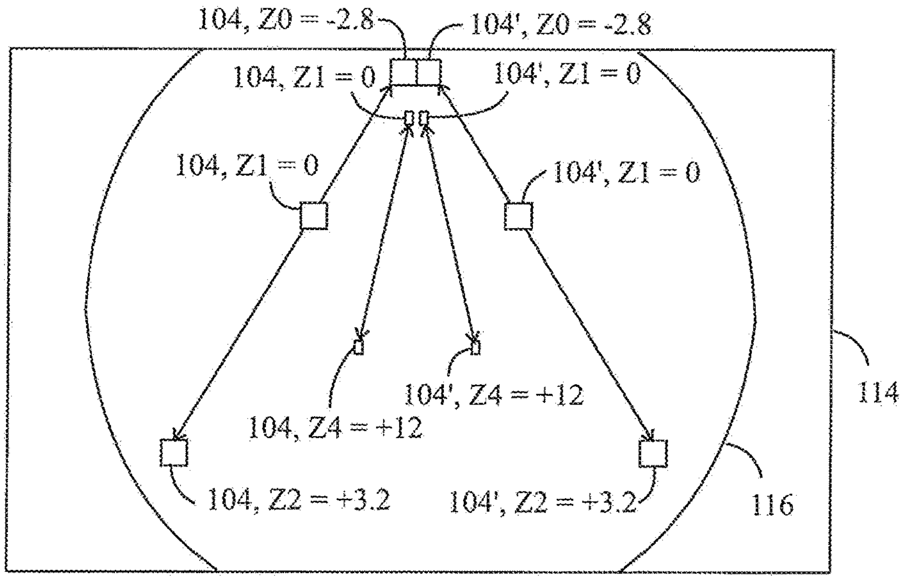
FIG. 10 illustrates an example of movements of the reflections of beams from the cornea on a detecting surface.

FIG. 10 illustrates an example how reflections of the beams 104, 104' change places on the detecting surface 114 as a function of a distance between the eye 120 and the ophthalmic examination apparatus 100 according to the examples of FIGS. 6 to 9.

In an embodiment, the alignment light generator 102 may generate two sets of the beams 104, 104' which are configured to operate in different alignment range AR. The first set of the beams 104, 104' may be configured as described in FIGS. 8 and 9, and the second set of the beams 104, 104' may be configured as described by FIGS. 6 and 7. In that manner, the first set of the beams 104, 104' may be used to obtain eye alignment information further away from the examination location 118 than the second set of the beams 104, 104'. On the other hand, the second set of the beams 104, 104' may be used to obtain more accurate alignment information close to the examination location 118 than can be obtained by the first set of the beams 104, 104'.

In an embodiment the alignment light generator 102 may generate the beams 104, 104' which are used to obtain eye alignment information, and in addition to that, the examination apparatus 100 comprises a camera which is used to capture video from the iris of the eye 120 during the alignment. The video may then be used to give additional eye alignment information. The camera system may be configured to give a rough position of the eye 120 in larger alignment range AR than the beams 104, 104', whereas the beams 104, 104' may be used to obtain more accurate eye positioning information closer to the examination location 118.

Figure 5B:
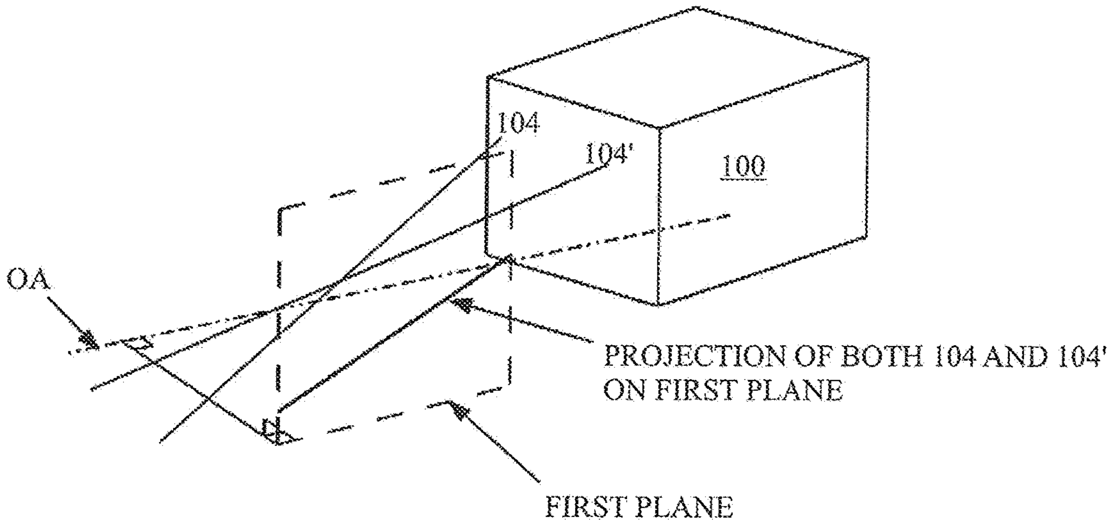
FIG. 5B illustrates an example where an alignment light generator directs the beams of light to the cornea in a particular manner.

In an embodiment, an example of which is shown in FIG. 5B, the alignment light generator 102 may direct the beams 104, 104' of light, which are parallel in a first plane i.e. whose projections on a first plane are parallel, a normal of which is perpendicular to an optical axis of the imaging unit 110, to the cornea 116 (note the model of the eye explained earlier in this document) so that the lines along the cornea reflected beams pass through an image 112 of the aperture stop 108 of the imaging unit 110 when the eye 120 is located in the alignment range AR.

In an embodiment, the alignment light generator 102 may direct the beams 104, 104' of light, which are parallel in a second plane a normal of which is perpendicular to an optical axis OA of the imaging unit 110 to the cornea 116 so that the lines along the beams reflected from the cornea 116 pass through the image 112 of the aperture stop 108 of the imaging unit 110 when the eye 120 is located in the alignment range AR, the normal of the first plane and the normal of the second plane being non-parallel.

In an embodiment, the alignment light generator 102 may direct the beams 104, 104' of light, which are parallel in a first plane, a normal of which is perpendicular to an optical axis of the eye 120, which is aligned in the examination location 118, to the cornea 116 so that the lines that are virtual continuations of the beams reflected from the cornea 116 pass through an image 112 of the aperture stop 108 of the imaging unit 110 when the eye 120 is located in the alignment range AR.

In an embodiment an example of which is illustrated in FIG. 5A, the alignment light generator 102 may direct or distribute the beams 104, 104' of light symmetrically about the optical axis OA of the imaging unit 110 and make the beams 104, 104' of light to intersect each other at the examination location 118 of the ophthalmic examination apparatus 100. The alignment light generator 102 may make the beams 104, 104' of light to intersect each other at the cornea 116 of the eye 120 when the eye 120 is located at the examination location 118.

FIG. 5A illustrates an example of a cross section of the envelope 105, a normal of the cross section being perpendicular to propagation of the beams 104, 104' and the optical axis OA of the imaging unit 110. In FIG. 5A, beams of light that are shown using a dashed line are not distributed about the optical axis OA of the imaging unit 110 which is also a possibility in an embodiment.

Figure 13:
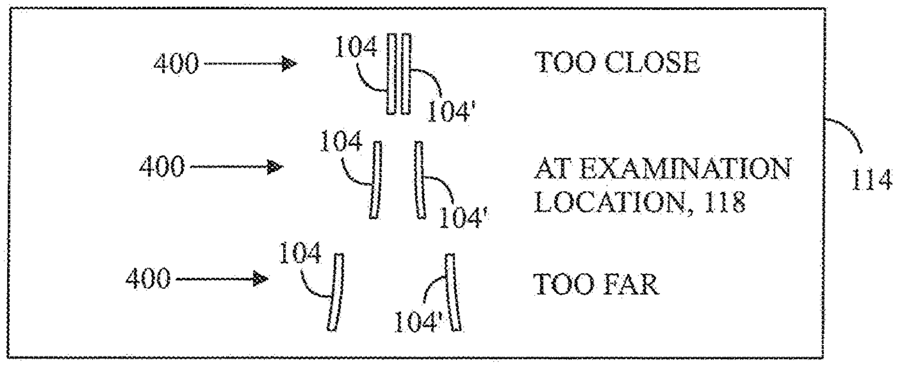
FIG. 13 illustrates an example of reflections of the oblique beams from the cornea on a detecting surface.

In an embodiment, the imaging unit 110 may cause at least one change of the direction of the reflections of the beams 104, 104' of light on the detecting surface 114 (see FIG. 13). In an embodiment, the at least one change of the directions of the reflections of the beams 104, 104' and the locations of spots 400 of light is performed by changing at least one direction of the beams 104, 104' of light that is transmitted from the alignment light generator 102. In an embodiment, the at least one change of the direction(s) is performed in response to movement of the eye 120 between opposite limits of the alignment range AR, the movement of the eye 120 being expected, potential, intentional, random or some combination of them.

In an embodiment, the imaging unit 110 may cause the at least one change of the locations of the reflections of the beams 104, 104' of light on the detecting surface 114 in response to the movement of the eye 120 between opposite limits of the alignment range AR in a direction parallel to the optical axis OA of the imaging unit 110.

In an embodiment, the alignment light generator 102 may output at least two beams 104, 104' of light and direct the at least two beams 104, 104' in a non-symmetrical manner, and the processing unit 126 of the ophthalmic examination apparatus 100 may compute a position of the eye 120 three-dimensionally with respect to the examination location 118 and a curvature of the cornea 116 of the eye 120.

In an embodiment, the ophthalmic examination apparatus 100 comprises three or more beams 104, 104' for computing a position of the eye 120 and the curvature of the cornea 116 of the eye 120. The three or more beams 104, 104' may be used to compute a gradient of a surface of the cornea 116.

In an embodiment, the processing unit 126 of the ophthalmic examination apparatus 100 may compute a distance of the eye 120 from the examination location 118 in a direction parallel to the optical axis OA of the imaging unit 110.

Figure 11:
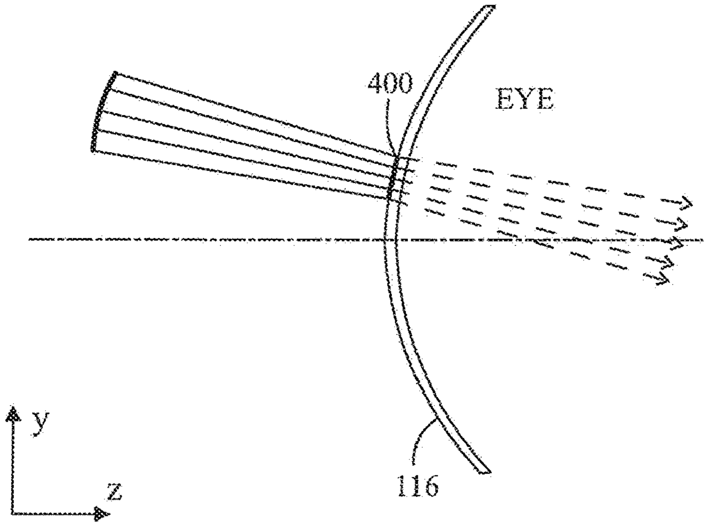
FIG. 11 illustrates an example of an oblique beam in an yz-plane.
Figure 12:
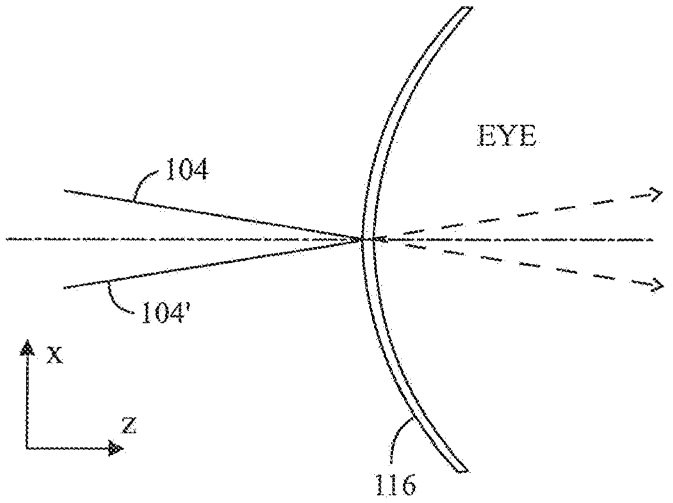
FIG. 12 illustrates an example of the oblique beam in an xz-plane.

In an embodiment on example of which is illustrated in FIGS. 11 and 12, a cross section of at least one of the beams 104, 104' of light is oblong. The beam 104 does not come from a point source and a width of the beam 104 in the y-direction is larger than in the x-direction, for example. The beams 104, 104' are overlapped in FIG. 11. As FIG. 12 illustrates, the beams 104, 104' are narrower in the y-direction, each of them is like a single ray or a narrow collimated beam, and in FIG. 12 they can be seen separately. In this manner, the beam forms an oblong spot 400 on the cornea 116. The oblong spot 400 may be a line of a certain length, for example. The line may be straight or curved. This kind of arrangement increases a length of the alignment range AR, because when the eye 120 is in the examination location 118 the line or the oblong spot 400 is fully on the detecting surface 114 of the imaging unit 110. When the eye 120 goes increasingly further away from the examination location 118, a decreasingly shorter section of the line or the oblong spot 400 is on the detecting surface 114. However, because the oblong spot 400 has larger length in one direction than in another direction, the oblong spot 400 can be detected in a larger alignment range AR. In an embodiment, the beam 104 and/or 104' has a larger dimension of in the y-direction than in the x-direction. In this embodiment, the y-direction may be vertical and the x-direction may be horizontal.

FIG. 13 illustrates the reflections of the beams 104, 104', which are the oblong spots 400 of light, on the detecting surface 114 in response to three different distances between the eye 102 and the ophthalmic examination apparatus. In general, the spots 400 of light may have various shapes. When the distance between the eye 120 and the ophthalmic examination apparatus 100 is too long, the oblong spots 400 of the beams 104, 104' are too far from each other. When the distance between the eye 120 and the ophthalmic examination apparatus 100 is correct and the eye 102 is at the examination location 118, the oblong spots 400 of the beams 104, 104' have a predefined distance therebetween. They may overlap or they may have a non-zero spacing in a known and desired manner. When the distance between the eye 120 and the ophthalmic examination apparatus 100 is too short, the oblong spots 400 of the beams 104, 104' are too close to each other. The position of the beams 104, 104' in the vertical direction is less important in FIG. 13, because the oblong spots 400 have been separated in the vertical direction due to clarity.

Figure 14:
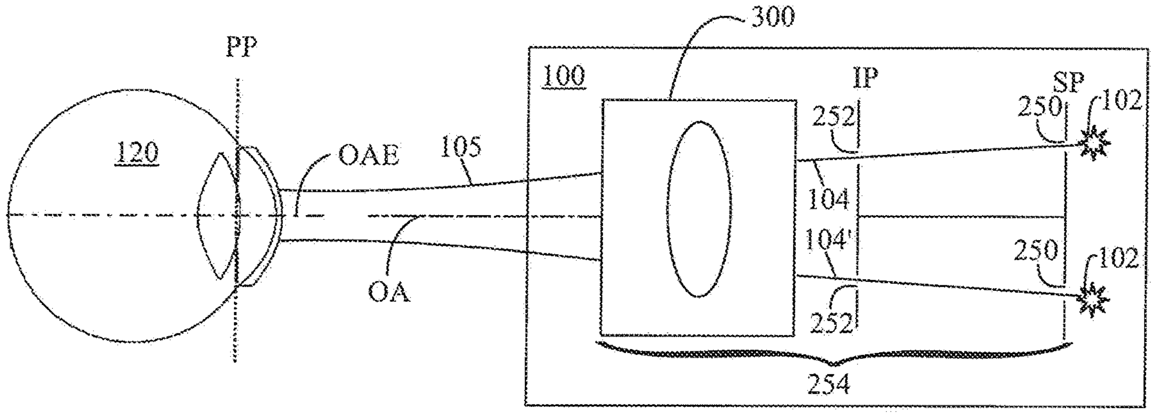
FIG. 14 illustrates an example of formation of the beams.

FIG. 14 illustrates an example of an embodiment, where the beams 104, 104' are formed initially or completely without an image forming optical component such as a lens. Here apertures 252 of an imaging plane IP creates the beams 104, 104' together with apertures 250 of a source plane SP by allowing light pass only through the apertures 250, 252 successively located in the direction of propagation of light from the alignment light generator 102. The source plane SP and the imaging plane IP may be considered a light manipulation arrangement 254. In an embodiment, light that passes through one aperture 250 of the source plane SP is only allowed to go through one aperture 252 of the imaging plane IP (see horizontal line illustrating a wall between the source plane SP and the imaging plane IP).

In some embodiments of FIG. 14, the light manipulation arrangement 254 may comprise the at least one image forming optical component 300, which forms an image of an imaging plane IP on the retina of the eye 120. However note that the at least one image forming optical component 300 is not always necessary but the apertures 150, 152 alone may direct the beams 104, 104' toward the alignment range AR. The image forming optical component 300 may form an image of a source plane SP approximately to the cornea 116 of the eye 120 which is located at the examination location 118 with respect to the ophthalmic examination apparatus 100.

When the at least one image forming optical component 300 is used, the image of the imaging plane IP may be in focus or it may be out-of-focus on the retina 116 when the examination is performed within the alignment range AR and/or at the examination location 118. Similarly, the image of the source plane SP may be in focus or it may be out-of-focus on the cornea 116. The image forming component 300 may comprise at least one lens or at least one image forming mirror, for example. The at least one image forming component 300 may refract the beams 104, 104' such that their envelope 105 converges to and diverge from the waist W, which is within an alignment range AR at a distance from the ophthalmic examination apparatus 100, where the distance may be known. The optical axis OAE of the eye 120 and the optical axis OA of the imaging unit 110 may be at least approximately aligned when the eye 120 is at the examination location 118 with respect to the ophthalmic examination apparatus 100.

In an embodiment, the ophthalmic examination apparatus 100 may capture a still image and/or a video of the eye 120 with the imaging unit 110. The still image and/or the video may be captured from the retina, cornea, crystalline lens or the like, for example.

In an embodiment, the ophthalmic examination apparatus 100 comprises a separate examination unit 110', which may capture a still image or a video of the eye 120 in a similar manner to the imaging unit 110.

Figure 15:
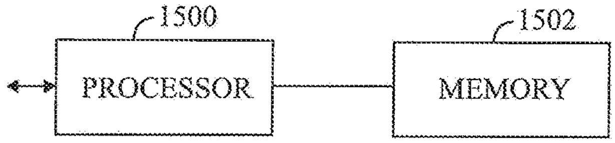
FIG. 15 illustrates an example of a data processing unit.

FIG. 15 illustrates an example of the data processing unit 126 of the ophthalmic examination apparatus 100. The data processing unit may comprise one or more processors 1500 and one or more memories 1502 including computer program code. The one or more memories 1502 and the computer program code with the one or more processors 1500 may cause the ophthalmic examination apparatus 100 to cause processing unit 126 at least to feed the guidance information to the user interface 128 for presenting the guidance information.

Now the operation of the alignment method is described by using simplified mathematical description. The mathematical formulation contains several approximations of different parameters and relations, which however must not be interpreted as limitations, but need to be understood as simplifications for clarity of the description.

Figure 16:
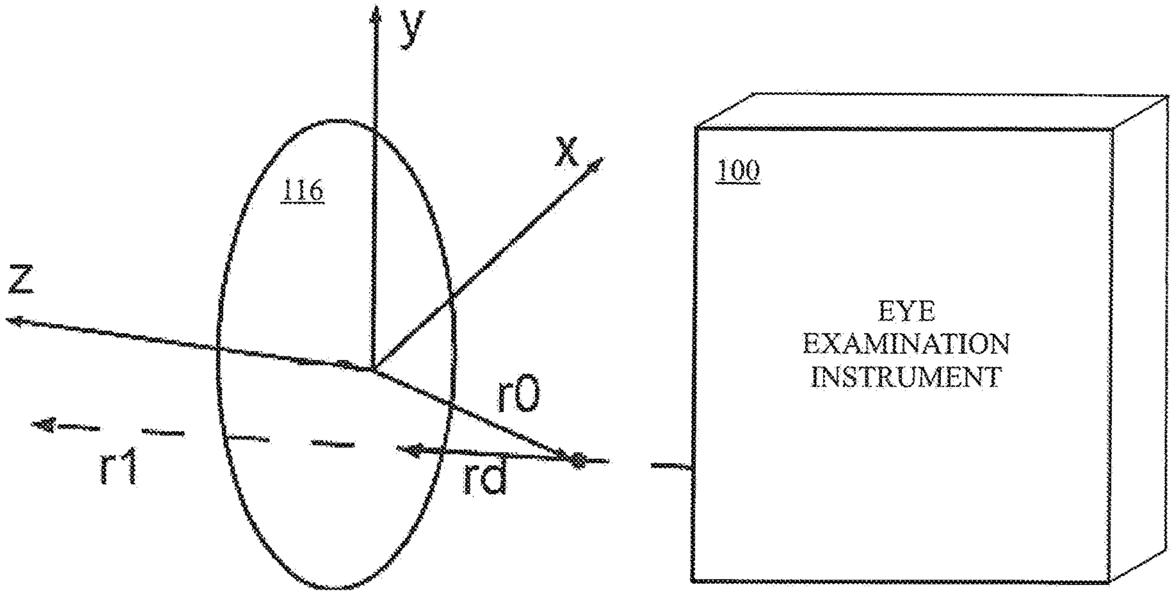
FIG. 16 illustrates an example of an eye-front-coordinates.

FIG. 16 shows a cornea 116 of an eye 120 at the examination location 118 in front of the ophthalmic examination apparatus 100. Let optical axis OAE of the eye 120 be approximately the same as a rotational symmetry axis of the cornea 116. It is possible to define an "eye-front coordinates" EFC by setting the origin PO at a predetermined position in respect to the examination location 118, setting the z-axis parallel to the optical axis OAE of the eye 120 and be directed toward the direction where OAE propagates through cornea 116 into the eye 120. In this example, the x-axis may be horizontal perpendicular to the z-axis, and the y-axis may be vertical. The xyz-axes may form an orthogonal right-handed coordinate system. The position and the orientation of this xyz-coordinate system (EFC) is then fixed by the nominal eye alignment, where the eye 120 is at the examination location 118.

A ray, which may represent a ray in a beam 104, 104' (for example, a central ray of a beam 104, 104'), propagating in a positive direction with respect to the z-axis of the EFC, may be defined in the EFC by:

$$r=r_0+t*r_d,$$

where $r_0$ is a point vector, $r_d$ is a direction vector, and t is a real number. Here, the vector $r_0$ points from a center of the cornea 116 or a pupil of the eye 120 to a point at a propagation path of light of a beam or a ray from the ophthalmic examination apparatus 100. The vector $r_d$, in turn, points to the direction of the propagation of light of the beam or the ray of the beam.

If the ray gets reflected from cornea 116, the resulting ray may be expressed similarly by:

$$r'=r_0'+t*r_d',$$

where $r_0'$, may be a point vector at ray intersection point with cornea 116, for example.

The intersection point $[x_j; y_j; z_j]$ of the ray r with any plane P parallel to xy-plane can be expressed as:

$$x_j=k_x z_j+b_x$$

$$y_j=k_y z_j+b_y \quad (1)$$

where $k_x=r_d(1)/r_d(3)$ and $k_y=r_d(2)/r_d(3)$ and $b_x$ and $b_y$ are x- and y-coordinates of the intersection points of the ray with the xy-plane of the EFC.

Figure 17:
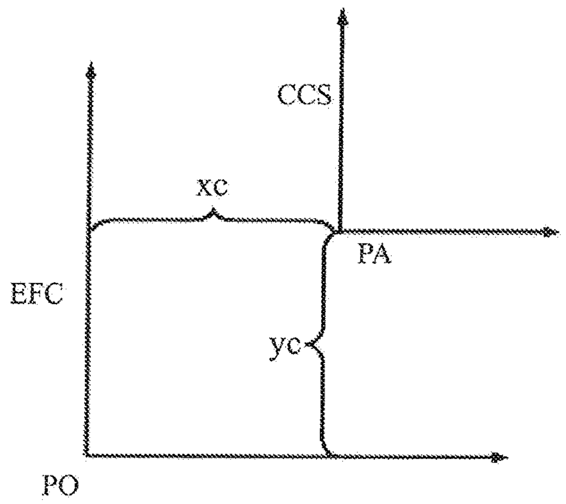
FIG. 17 illustrates an example of a cornea-coordinate system.
Figure 18:
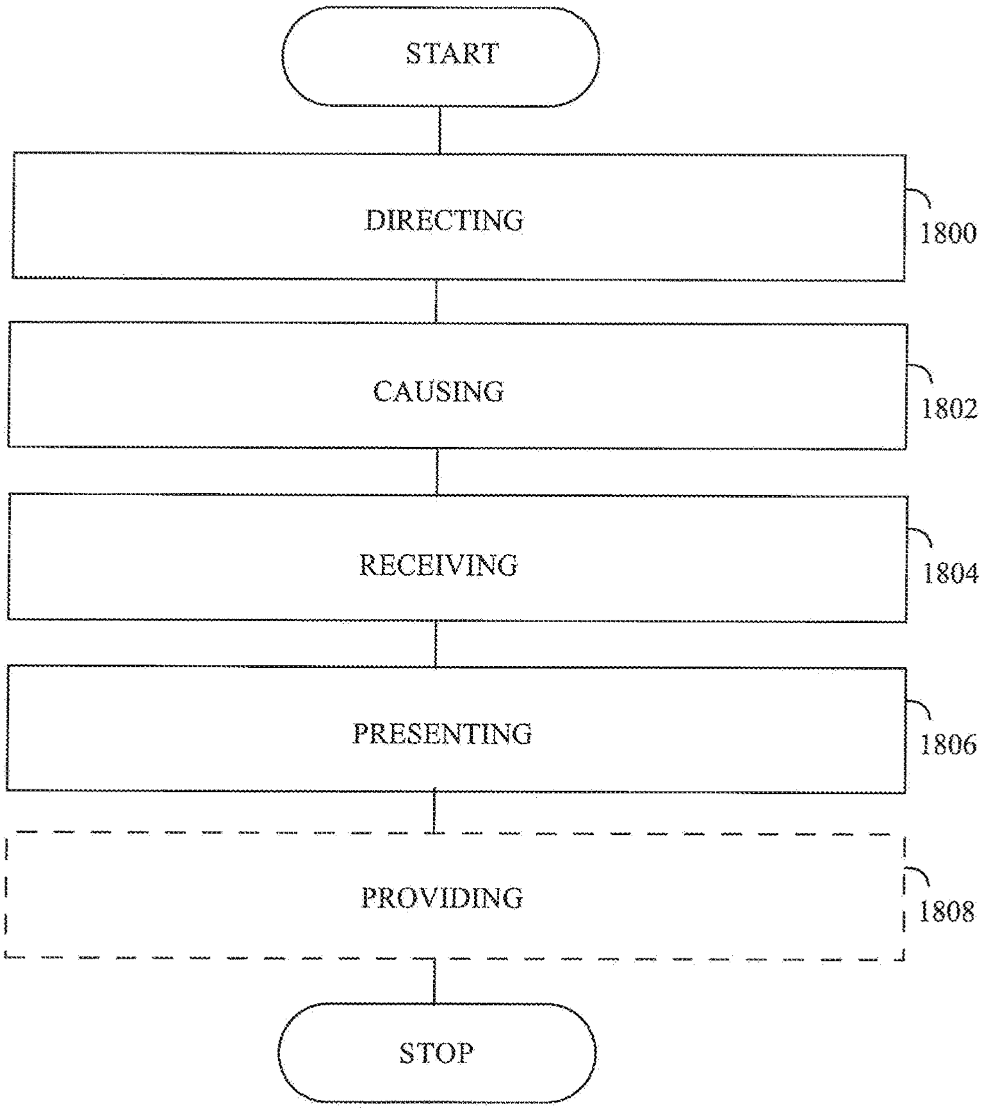
FIG. 18 illustrates of an example of a flow chart of an aligning method.

FIG. 17 illustrates an example of a cornea-coordinate-system, CCS. Assume now that the eye 120 moves from the examination location 118 to some arbitrary position. Assume also that a gaze direction is unchanged from that of the examination location 118 (we can roughly assume that a fixation target keeps the eye 120 to gaze at the same direction during this movement). The cornea-coordinate-system CCS can be defined in a similar manner to the EFC, but it moves with the eye 120 such that its origin PA is at cross-section of the cornea 116 and the optical axis OAE of the eye 120, and its axis are parallel to EFC coordinate system. The origin PA of the CCS has coordinates $[x_c; y_c; z_c]$ in the EFC, and the purpose of the xyz-alignment is to guide the PA to its nominal location such that the eye 120 is at the examination location 118.

The ophthalmic examination apparatus 100 comprises the imaging unit 110, and a sensor with the detecting surface 114. For simplifying the following exemplary mathematical description, assume that the imaging unit 110 and the detecting surface 114 are arranged in an approximately conoscopic arrangement. In such an arrangement, a position of a ray/beam 104, 104' on the detecting surface 114 can be defined by the direction of the ray/beam 104, 104' only before the imaging unit 110; this can simply be achieved by set-up where the detecting surface 114 is positioned at the focal plane of the imaging unit 110, for example. Assume further that a ray r' reflected from the cornea 116 is captured by the imaging unit 110 and guided to the detecting surface 114. The position of the ray on the detecting surface 114 depends approximately only from $r_d'$ but not from $r_0'$.

For simplicity of the following mathematical description, assume a relatively narrow beam 104, 104' which may be represented by its central ray r, and assume that a shape of the cornea 116 may be approximated to be spherical. However, note that these approximations are not necessary for the operation of the alignment described in this document.

In the CCS, the cornea sag can be expressed by equation $$z = r_c - \sqrt{r_c^2 - x^2 - y^2},$$

where $r_c$ is a cornea radius of the curvature (approximately 7.8 mm with emmetropic eye. i.e. a standard eye), and x and y are coordinates in CCS along x- and y-axis.

From this it is possible express the cornea surface angle along the x-axis as:

$$\frac{dz}{dx} \approx x\frac{A(r_c)}{2},$$

and along y as $$\frac{dz}{dy} \approx y\frac{A(r_c)}{2},$$

where $A(r_c)>0$ is a coefficient which depends on the cornea radius $r_c$.

For simplicity, it is possible to approximate that the ray intersection point with the cornea 116 is at the ray intersection point with the xy-plane going through a cornea apex, i.e. the ray r intersects the cornea 116 at a point $[x_j; y_j; z_j]$ in the EFC, where $x_j=x_c+x_i$, $y_j=y_c+y_i$ and $z_j=z_c+z_i$, where $[x_i; y_i; z_i]$ is the intersection point in the CCS.

Now, it is possible to approximate the x- and y-components of a direction vector of a ray or the beam 104, 104' reflected from the cornea 116 to be $$r_d'(1) = -r_d(1) + A(r_c)x_i, \text{ and}$$

$$r_d'(2) = -r_d(2) + A(r_c)y_i.$$

It is possible to define the coordinate system, at the sensor such that the coordinate values of the ray or the beam 104, 104' on the detecting surface 114 are approximately the same as the x- and y-components of its direction vector $r_d'$ in the EFC multiplicated by a scaling factor K, i.e.:

$$s = \begin{bmatrix} S_x \\ S_y \end{bmatrix} = \begin{bmatrix} Kr_d'(1) \\ Kr_d'(2) \end{bmatrix} = \begin{bmatrix} K(-r_d(1) + A(r_c)x_i) \\ K(-r_d(2) + A(r_c)y_i) \end{bmatrix}$$

from which, after combining with Equation (1) it is possible to deduce the following two equations:

$$\begin{cases} k_x z_c - x_c + 0 - \dfrac{s_x}{A(r_c)K} = \dfrac{k_x}{A(r_c)} - b_x \\ k_y z_c + 0 - y_c - \dfrac{s_y}{A(r_c)K} = \dfrac{k_y}{A(r_c)} - b_y \end{cases} \tag{2}$$

This pair of equations (2) can be used to solve a cornea position $[x_c; y_c; z_c]$ from positions of the beams 104, 104' on the detecting surface 114 $[s_x; s_y]$ by different ways.

The equation pair (2) has 11 variables, five of which are potentially known properties of the instrument ($k_x$, $k_y$, $b_x$, $b_y$, K), one is property of the eye 120 ($A(r_c)$), and the rest five are properties of alignment and vary during the eye alignment ($x_c$, $y_c$, $z_c$, $s_x$, $s_y$). The variables $s_x$ and $s_y$ are coordinates of the locations of the beams 104, 104' reflected from the cornea 116 on the detecting surface 114 and are always known when the beams 104, 104' hit the detecting surface 114.

The values for the properties ($k_x$, $k_y$, $b_x$, $b_y$, K) of the ophthalmic examination apparatus 100 may be known by calibration of the ophthalmic examination apparatus 100. It has also been found out that the curvature of the cornea 116 may vary considerable between patients. Therefore when accurate alignment is needed, either the effect of $A(r_c)$ needs to be eliminated from the process, or it needs to be solved with sufficient accuracy during the alignment process.

Since there are altogether four unknown variables ($A(r_c)$, $x_c$, $y_c$ and $z_c$), four linearly independent equations needs to be written. This can be done by using two reflected rays 104, 104' from the cornea 116 such that for each location of the beams 104, 104' on the detecting surface 114 the equation (2) is written. This can be presented using the following group of equations below:

$$\begin{cases} k_{x,1}z_c - x_c + 0 - \frac{s_{x,1}}{A(r_c)K} = \frac{k_{x,1}}{A(r_c)} - b_{x,1} \\ k_{y,1}z_c + 0 - y_c - \frac{s_{y,1}}{A(r_c)K} = \frac{k_{y,1}}{A(r_c)} - b_{y,1} \\ k_{x,2}z_c - x_c + 0 - \frac{s_{x,2}}{A(r_c)K} = \frac{k_{x,2}}{A(r_c)} - b_{x,2} \\ k_{y,2}z_c + 0 - y_c - \frac{s_{y,2}}{A(r_c)K} = \frac{k_{y,2}}{A(r_c)} - b_{y,2} \end{cases}$$

where notations 1 and 2 represent different beams 104, 104' ($k_{x,1}$ is x-angle component of ray 1 and $k_{x,2}$ is a corresponding component for ray 2). Here each $k_x$, $k_y$, $b_x$ and $b_y$ and by may be determined and the positions of the beams 104, 104' on the detection surface 114 $s_x$ and $s_y$ may be measured before this equation group is solved. Equations may be rewritten in the matrix form:

$$A\begin{bmatrix} x_c \\ y_c \\ z_c \\ \frac{1}{A(r_c)} \end{bmatrix} = -\begin{bmatrix} b_{x,1} \\ b_{y,1} \\ b_{x,2} \\ b_{y,2} \end{bmatrix}$$

where $$A = \begin{bmatrix} -1 & 0 & k_{x,1} & -\left(\frac{s_{x,1}}{K} + k_{x,1}\right) \\ 0 & -1 & k_{y,1} & -\left(\frac{s_{y,1}}{K} + k_{y,1}\right) \\ -1 & 0 & k_{x,2} & -\left(\frac{s_{x,2}}{K} + k_{x,2}\right) \\ 0 & -1 & k_{y,2} & -\left(\frac{s_{y,2}}{K} + k_{y,2}\right) \end{bmatrix}$$

Here the matrix in the left side contains only measured parameters, and the unknown variables $x_c$, $y_c$, $z_c$ and $$\frac{1}{A(r_c)}$$

can De solved oy operating me equations with the inverse matrix of the A in the following manner:

$$\begin{bmatrix} x_c \\ y_c \\ z_c \\ \frac{1}{A(r_c)} \end{bmatrix} = -A^{-1}\begin{bmatrix} b_{x,1} \\ b_{y,1} \\ b_{x,2} \\ b_{y,2} \end{bmatrix}$$

Note that this requires that the matrix A must have an inverse matrix and thus a determinate of the matrix A may not be zero, which can easily be avoided by a proper selection of the coordinate system.

In an embodiment, two substantially yz-symmetric alignment beams 104, 104' may be used, and they may intersect each other at the cornea 116 when cornea the is at the examining location 118.

Referring to the central rays of the two beams 104, 104' with sub-indices 1 and 2, in the case of Equation (2), the following approximations may be formed and found valid:

$b_{x,1}=b_{y,1}=b_{x,2}=b_{y,2}=0$ (due to the symmetry, and as we can set the EFC origin to the intersection point of the beams 104, 104' without loss of generality)

$k_{y,1}=k_{y,2}$ and $k_{x,1}=-k_{x,2}$, due to the symmetry on the detection surface 114: $s_{y,1}=s_{y,2}$, due to the symmetry both location of the beams 104, 104' on the detecting surface 114 move similarly in a vertical dimension.

It is also possible to form the following four equations:

$$\begin{cases} k_x z_c - x_c + 0 - \frac{s_{x,1}}{A(r_c)K} = \frac{k_x}{A(r_c)} & \text{(A1)} \\ k_y z_c + 0 - y_c - \frac{s_y}{A(r_c)K} = \frac{k_y}{A(r_c)} & \text{(A2)} \\ -k_x z_c - x_c + 0 - \frac{s_{x,2}}{A(r_c)K} = -\frac{k_x}{A(r_c)} & \text{(A3)} \\ k_y z_c + 0 - y_c - \frac{s_y}{A(r_c)K} = \frac{k_y}{A(r_c)} & \text{(A4)} \end{cases}$$

Equations (A2) and (A4) are identical so there is infinite amount of solutions. However, if the distance D between the locations on detection surface 114 are measured in the x-direction, it is possible to get the x-distance between the locations of the beams 104, 104' from equations (A1) and (A3):

$$D = s_{x,1} - s_{x,2} = 2Kk_x(1 - A(r_c)z_c) \tag{13}$$

from which it is possible to solve $$z_c = \left(1 - \frac{D}{2Kk_x}\right)\frac{1}{A(r_c)}.$$

As the EFC origin is set to the beams 104, 104' intersection points at the cornea 116 when the eye 120 is at the examination location 118, the variable $z_c$ becomes approximately the distance of the eye 120 along the z-axis from the examination location 118, which is positive or negative depending on which side of the examination position the eye 120 is.

The variable $z_c$ has the following properties:

the distance of the reflection of the beams 104, 104' on the detecting surface 114 has a unique value $D_0=2Kk_x$ only when $z_c=0$, i.e. when the eye 120 is at the examination location 118 the variable $z_c$ is independent of a shape of the cornea 116, i.e. the factor $A(r_c)$, and the obtained value of the variable $z_c$ has a correct sign, i.e. the $z_c$ value can be used to guide the eye 120 to the examination location 118 the deviation of the distance from the value $D_0$ is directly proportional to value of the variable $z_c$ In this manner, alignment instructions may be given by the x-distance between the locations of the reflections 1, 2 of the beams 104, 104' on the detecting surface 114.

From the equations A1)-A4) it is possible to see that when $z_c$ approaches zero (then cornea 116 approaches examination location 116), the $x_c$ and $y_c$ coordinates (x- and y-positions of the cornea 116) are linear functions of the locations of the reflections of the beams 104, 104' in the x- and y-coordinates on the detecting surface 114 ($s_{x,1}$, $s_{x,2}$, $s_y$) in the following manner:

$$x_c = -\frac{s_{x,1}}{A(r_c)K} - \frac{k_x}{A(r_c)} \rightarrow s_{x,1} = -x_cA(r_c)K - k_xK$$

-continued $$x_c = -\frac{s_{x,2}}{A(r_c)K} + \frac{k_x}{A(r_c)} \rightarrow s_{x,2} = -x_c A(r_c)K + k_x K$$

$$y_c = -\frac{s_y}{A(r_c)K} - \frac{k_y}{A(r_c)} \rightarrow s_y = -y_c A(r_c)K - k_y K$$

which means that a position of the eye 120 is correct in x-dimension, if $x_c=0$, i.e. when the two locations of the reflections of the beams 104, 104' are symmetrical in the x-distance $k_xK$ at different sides of the origin of the known sensor coordinate system (which can be found out by calibration)

y-dimension, when $y_c=0$, i.e. if the both locations of the reflections of the beams 104, 104' are at a predetermined y-position ($-k_yK$) in respect to the origin of the sensor coordinate system.

FIG. 8 is a flow chart of the alignment method. In step 1800, beams 104, 104' of light are directed with an alignment light generator 102 from separate locations 101, 103 toward an image 112 of an aperture stop 108 of an imaging unit 110 of the ophthalmic examination apparatus 100. The beams 104, 104' of light may be directed with the alignment light generator 102 from the separate locations 101, 103 toward the cornea of the eye 120 at the examination location 118, so that the central axis of the beams cross the image 112 of the aperture stop 108 of an imaging unit 110 of the ophthalmic examination apparatus 100.

In step 1802, an envelope 105 of the beams 104, 104' of light is caused to converge to and diverge from a waist W, which is within an alignment range AR of the ophthalmic examination apparatus 100, an eye 120 being at an examination location 118 with respect to the imaging unit 110 in response to a waist W of the envelope 105 being located at least partly inside a pupil 122 of the eye 120, the ophthalmic examination apparatus 100 having the examination location 118 within the alignment range AR. The cornea 116 being within the alignment range AR with respect to the waist W.

In step 1804, receiving 1804, reflections of the beams 104, 104' of light are received with the imaging unit 110 from a cornea 116 of the eye 120 when the eye 120 similar to a standard eye within standard tolerances is within the alignment range AR.

In step 1806, guidance information based on the locations of the reflections of the beams 104, 104' of light on the detecting surface 114 of the imaging unit 110 is presented by a user interface 128 of the ophthalmic examination apparatus 100.

In step 1808, which is optional, a processing unit 126 of the ophthalmic examination apparatus 100 provides with the guidance information based on the locations of the reflections of the beams 104, 104' of light on the detecting surface 114 of the imaging unit 110.

The method and its step 1808 shown in FIG. 8 may be implemented as a logic circuit solution or computer program. The computer program may be placed on a computer program distribution means for the distribution thereof. The computer program distribution means is readable by a data processing device, and it encodes the computer program commands, carries out the computation and provision of the guidance information and optionally controls the ophthalmic examination apparatus 100.

The computer program may be distributed using a distribution medium which may be any medium readable by the controller. The medium may be a program storage medium, a memory, a software distribution package, or a compressed software package. In some cases, the distribution may be performed using at least one of the following: a near field communication signal, a short distance signal, and a telecommunications signal.

What is taught in this document results in an improved alignment between the eye that is examined and an ophthalmic examination apparatus with potentially the following advantages:

improved alignment accuracy faster alignment suitability with autonomous instruments improved patient and/or user experience.

It will be obvious to a person skilled in the art that, as technology advances, the inventive concept can be implemented in various ways. The invention and its embodiments are not limited to the example embodiments described above but may vary within the scope of the claims.

The invention claimed is:

1. An ophthalmic examination apparatus, which comprises an alignment light generator, wherein the alignment light generator is configured to direct beams of light, a cross section of at least one of which is oblong, from separate locations toward an image of an aperture stop of an imaging unit of the ophthalmic examination apparatus, the image of the aperture stop of the imaging unit being in front of the ophthalmic examination apparatus, and cause an envelope of the beams of light to converge to and diverge from a waist, which is within an alignment range of the ophthalmic examination apparatus, an eye being at an examination location with respect to the imaging unit in response to the waist of the envelope being located at least partly inside a pupil of the eye, the ophthalmic examination apparatus being configured to have the examination location within the alignment range;

wherein the imaging unit is configured to receive reflections of the beams of light from a cornea of the eye within the alignment range, the eye being similar to a standard eye within standard tolerances;

wherein a user interface of the ophthalmic examination apparatus is configured to present, directly or indirectly guidance information on a location of the eye with respect to the examination location based on locations of the reflections of the beams of light on a detecting surface of the imaging unit; and wherein the imaging unit is further configured to cause the at least one change of the locations of the reflections of the beams of light on the detecting surface in response to the movement of the eye between opposite limits of the alignment range in a direction parallel to the optical axis of the imaging unit.

2. The apparatus of claim 1, wherein the alignment light generator is configured to direct the beams of light via a beam splitter toward the image of the aperture stop.

3. The apparatus of claim 1, wherein the alignment light generator is configured to direct the beams of light, projections of which are parallel in a first plane, a normal of which is perpendicular to an optical axis of the imaging unit.

4. The apparatus of claim 1, wherein the alignment light generator is configured to direct the beams of light symmetrically about the optical axis of the imaging unit and make beams of light to intersect each other at the examination location of the ophthalmic examination apparatus.

5. The apparatus of claim 1, wherein the processing unit of the ophthalmic examination apparatus comprises one or more processors;

one or more memories including computer program code; and a user interface;

wherein the one or more memories and the computer program code are configured to, with the one or more processors, cause processing unit at least to feed the guidance information to the user interface for presenting the guidance information.

6. The apparatus of claim 5, wherein the alignment light generator is configured to direct at least two of the beams of light in a non-symmetrical manner, and the processing unit of the ophthalmic examination apparatus is configured to compute a position of the eye three-dimensionally with respect to the examination location and a curvature of the cornea of the eye.

7. The apparatus of claim 5, wherein the processing unit of the ophthalmic examination apparatus is configured to compute a distance of the eye from the examination location in a direction parallel to the optical axis of the imaging unit.

8. The apparatus of claim 1, wherein the alignment light generator is configured to output the beams of light that are in an infrared region.

9. The apparatus of claim 1, wherein the ophthalmic examination apparatus is a fundus camera.

10. The apparatus of claim 1, wherein the ophthalmic examination apparatus is configured to capture a still image or a video of the eye with the imaging unit, and/or the ophthalmic examination apparatus comprises an examination unit, which is configured to capture a still image or a video of the eye.

11. An ophthalmic examination apparatus, which comprises an alignment light generator, wherein the alignment light generator is configured to direct beams of light, a cross section of at least one of which is oblong, from separate locations toward an image of an aperture stop of an imaging unit of the ophthalmic examination apparatus, the image of the aperture stop of the imaging unit being in front of the ophthalmic examination apparatus, and cause an envelope of the beams of light to converge to and diverge from a waist, which is within an alignment range of the ophthalmic examination apparatus, an eye being at an examination location with respect to the imaging unit in response to the waist of the envelope being located at least partly inside a pupil of the eye, the ophthalmic examination apparatus being configured to have the examination location within the alignment range;

wherein the imaging unit is configured to receive reflections of the beams of light from a cornea of the eye within the alignment range, the eye being similar to a standard eye within standard tolerances;

wherein a user interface of the ophthalmic examination apparatus is configured to present, directly or indirectly guidance information on a location of the eye with respect to the examination location based on locations of the reflections of the beams of light on a detecting surface of the imaging unit; and wherein a cross-sectional area of at least one of the beams at or adjacent to a waist is in a range from about 1 $mm^2$ to about 8 $mm^2$.

12. The apparatus of claim 1, wherein the cross section of at least one of the beams is substantially circular, elliptical, rectangular, or square.

13. The apparatus of claim 1, wherein the alignment light generator comprises at least one initial lens and at least one objective lens configured to collimate the beams and cause the envelope of the beams to converge to and diverge from the waist.

14. The apparatus of claim 5, wherein the near-infrared wavelength band is from about 750 nm to about 970 nm.

15. The apparatus of claim 1, wherein the alignment light generator comprises at least one light source selected from the group consisting of light-emitting diodes, organic light-emitting diodes, incandescent sources, and lasers, optionally with a band-pass filter.

16. The apparatus of claim 1, wherein the alignment light generator is configured to generate two sets of beams, a first set configured for a coarse alignment range and a second set configured for a fine alignment range.

17. The apparatus of claim 1, wherein the cross section of at least one of the beams is oblong such that a dimension in a first direction is larger than in a second direction, thereby increasing the alignment range.

18. The apparatus of claim 1, further comprising a camera configured to capture video of the iris of the eye during alignment to provide additional alignment information.

* * * * *